United States Patent
Brooks

(10) Patent No.: US 6,699,706 B1
(45) Date of Patent: Mar. 2, 2004

(54) CELL LYSIS METHOD USING A VORTEX MIXER

(75) Inventor: Robert Cecil Brooks, Blewbury (GB)

(73) Assignee: Accentus PLC, Didcot (GB)

( * ) Notice: Subject to any disclaimer, the term of this patent is extended or adjusted under 35 U.S.C. 154(b) by 411 days.

(21) Appl. No.: 09/323,990

(22) Filed: Jun. 2, 1999

(30) Foreign Application Priority Data

Jun. 13, 1998 (GB) .............................................. 9812713

(51) Int. Cl.$^7$ .......................... C12M 1/00; C12M 1/10; C12M 1/33; C12M 3/00; C12N 1/06
(52) U.S. Cl. ................. 435/259; 435/283.1; 435/298.1; 435/298.2; 435/306.1
(58) Field of Search ............................. 435/259, 283.1, 435/298.1, 298.2, 306.1, 820; 137/810, 811, 812; 210/787

(56) References Cited

U.S. PATENT DOCUMENTS

| | | | |
|---|---|---|---|
| 4,652,517 A | 3/1987 | Scholl | 435/5 |
| 4,775,622 A | 10/1988 | Hitzeman | 435/68 |
| 4,880,746 A | 11/1989 | Wohlleben | 435/253.5 |
| 5,047,345 A | 9/1991 | DeBonville | 435/270 |
| 5,096,818 A | 3/1992 | DeBonville | 435/91 |
| 5,437,985 A | 8/1995 | Quintana | 435/7.24 |
| 5,837,529 A | 11/1998 | Wan | 435/259 |

FOREIGN PATENT DOCUMENTS

| | | |
|---|---|---|
| EP | 0271667 | 6/1988 |
| EP | 0341215 | 11/1989 |
| EP | 0626456 | 11/1994 |
| FR | 1576299 | 7/1969 |
| GB | 2241796 | 9/1991 |
| WO | WO 91/01367 | 2/1991 |
| WO | WO 96/12956 | 5/1996 |

OTHER PUBLICATIONS

Michael Mutsakis and Robert Rader, "Static Mixers Bring Benefits to Water/Wastewater Operations," Water/Engineering & Management, Nov., 1986, pp. 30–31.

Primary Examiner—David M. Naff
Assistant Examiner—Deborah K. Ware
(74) Attorney, Agent, or Firm—William H. Holt

(57) ABSTRACT

Cell lysis may be brought about by contacting a suspension of cells with a lysis reagent such as sodium hydroxide solution; subsequent treatment enables organic molecules such as plasmid DNA to be separated from other cell components. Intimate mixing of the cell suspension with lysis reagent is achieved by passage through a fluidic vortex mixer arranged so the residence time of the cell suspension in the mixer is less than the time for lysis to be completed, and may be less than 0.1 seconds. Such a vortex mixer comprises a cylindrical chamber with an axial outlet duct and at least one tangential inlet duct, but with no internal baffles. The low shear stress to which the cell suspension is subjected minimizes loss of product through denaturation or fragmentation of the product, and indeed of contaminants. The subsequent treatment may also utilize a fluidic vortex mixer.

13 Claims, 1 Drawing Sheet

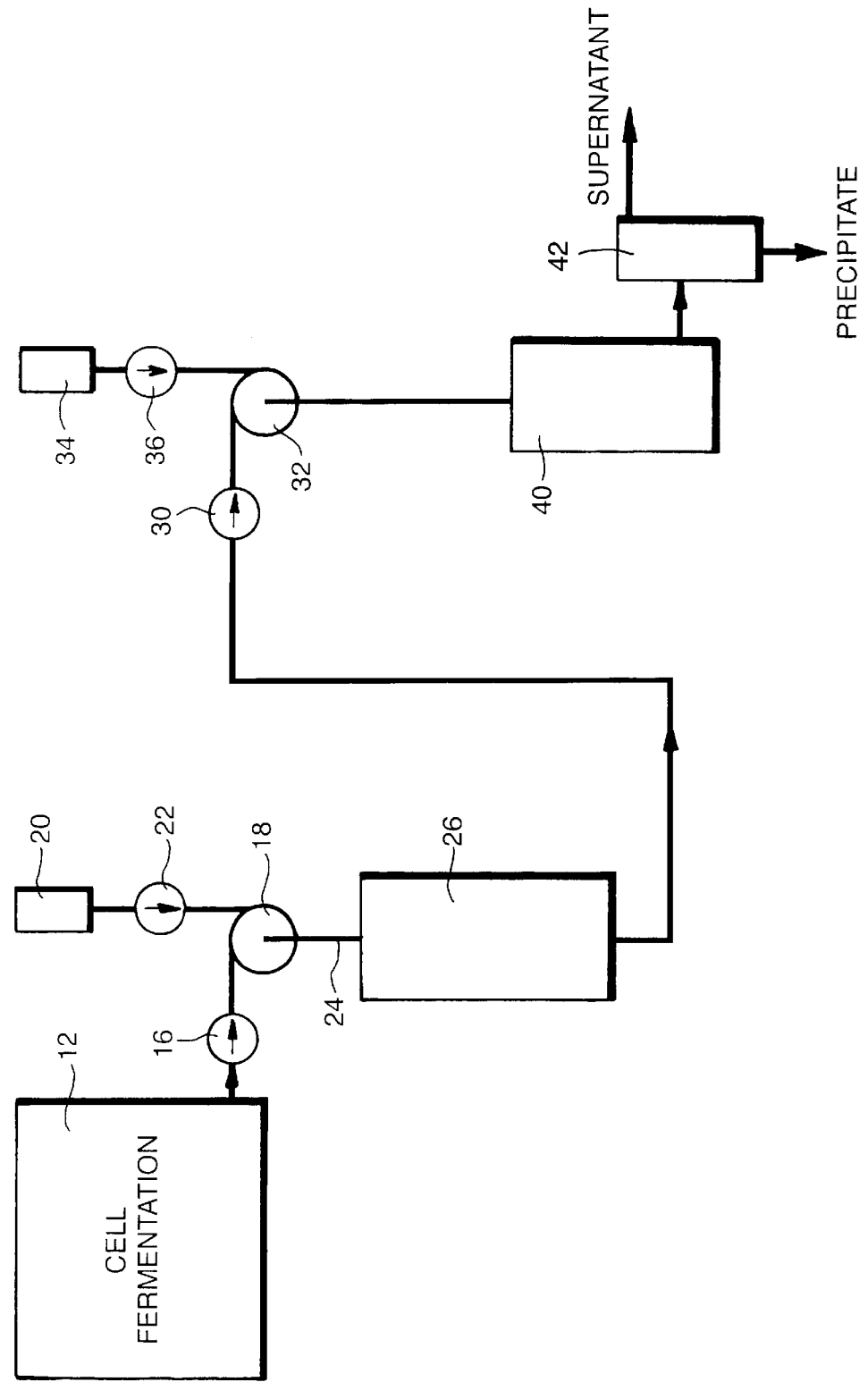

CELL LYSIS METHOD USING A VORTEX MIXER

This invention relates to a process for treating suspensions of microbiological cells, for example for performing cell lysis, and for treating the fluid produced as a result of cell lysis.

A range of complex organic molecules can be synthesised within cells, such as bacterial cells, in a fermentation process. The desired product molecules must then be recovered and purified from the cells. In many cases, for example the synthesis of genetic material in the form of plasmid DNA, this is achieved using an initial cell lysis step followed by subsequent processing to remove contaminants through techniques such as precipitation. Cell lysis may be brought about by contacting a suspension of the cells with a lysis reagent such as sodium hydroxide solution. The rate at which homogenous mixing can be achieved is crucial to optimal performance of the lysis reaction. If the rate of mixing is too slow then lysis will occur in discrete regions within the fluids held within the mixer. This will reduce the rate at which lysis agent is able to contact the cells suspended within the fluid, as local increases in viscosity will impede the efficiency of the mixing process. This may result in damage to the desired product as a result of prolonged exposure to shear forces induced by the mixer, and loss of product due to incomplete lysis of the cells, and it increases the possibility of fouling due to the formation of by-products from the lysis reagent cross reacting with other cell components released subsequent to lysis.

According to the present invention there is provided a method for processing cells wherein an aqueous suspension of cells is intimately mixed with a lysis reagent by passage through a fluidic vortex mixer, the dimensions of the mixer and the flow rates being such that the residence time of the cell suspension in the mixer is less than the time for lysis to be completed.

A fluidic vortex mixer comprises a substantially cylindrical chamber with an axial outlet duct at the centre of an end wall of the chamber, and with at least one substantially tangential inlet near the periphery of the chamber to create a spiralling flow in the chamber. A second liquid may be supplied through a second tangential inlet, or through a radial inlet. The chamber contains no vanes or baffles. Such a mixer achieves a very intimate mixing of the two liquids in a very short time, yet it does not subject the liquids to high shear. It is also much less prone to being fouled, for example by proteinaceous deposits, than other types of mixer.

The residence time means the time taken by the cell suspension to pass through the mixer. This is preferably much less than the time taken for lysis to be completed, and is preferably less than 0.1 seconds, more preferably less than 0.01 seconds, so that the emerging liquid mixture is of viscosity similar to that of the in-flowing cell suspension. In this specification 'completion of lysis' refers to both the breaking down of the cell walls and the resulting increase in viscosity as cellular proteins and chromosomal DNA released from the cells interact with the lysis reagent. Preferably the viscosity increases during passage through this mixer by a factor of no more than ten times, more preferably no more than five times, for example less than twice. The low shear stress to which the cell suspension is subjected minimizes loss of product through denaturation or fragmentation of the product, and indeed of contaminants. Furthermore the rapid, intimate mixing ensures that all the cells are subjected to optimal conditions for lysis to occur.

The cell processing procedure usually involves subsequent treatment of the lysed cells with a precipitation agent. The invention also envisages a mixture of cell suspension and lysis reagent being mixed with the precipitation agent by passage through a fluidic vortex mixer. This may be a second such vortex mixer. Alternatively the precipitation agent may be mixed with the mixture of cell suspension and lysis reagent during its passage through the first vortex mixer, by supplying the precipitation agent to a third inlet duct into the first vortex mixer; this third inlet duct preferably communicates with the outlet duct from the chamber, and the open end of this third inlet duct may be adjustable in its position along the axis of the outlet duct.

The invention will now be further and more particularly described by way of example only, and with reference to the accompanying drawing which shows a flow diagram for a cell product recovery system.

Referring to the drawing, a system 10 is shown for obtaining plasmid DNA. Bacteria (*Escherichia coli*) genetically engineered to make the desired plasmid DNA are grown in a fermentation vessel 12. When sufficient fermentation has taken place, an aqueous cell suspension is pumped from the vessel 12 by a low-shear pump 16 (such as a mono pump) to one tangential inlet of a fluidic vortex mixer 18. An aqueous solution of sodium hydroxide is supplied from a storage tank 20 via a pump 22 to a second tangential inlet of the vortex mixer 18. The resulting intimate mixture of cell suspension and sodium hydroxide emerges from an axial outlet 24 of the mixer 18; the residence time of the cell suspension in the mixer 18 is less than 0.1 seconds.

By way of exemplification, the flow rate through the mixer 18 might be one liter per minute, and the cylindrical chamber in the mixer 18 might be of diameter 10 mm and of height 2 mm, the two inlet ducts being of cross-sectional area 1 mm$^2$ and the outlet duct 24 of diameter 2 mm. This would provide a residence time of about 8 ms. If the flow rate through this mixer 18 were halved, to 0.5 liter/min, the mean residence time would be doubled, to about 16 ms.

The mixture from the outlet 24 is supplied to a tank 26, in which lysis is completed. The cell membranes break down, and open-strand DNA and RNA form complexes with each other and with proteins; consequently the mixture uniformly increases in viscosity. The tank has an outlet duct 28 at the bottom, the flow rates and the dimensions of the tank 26 being such that the residence time of the mixture in the tank 26 is sufficient to ensure lysis is complete, for example one minute, or 10 minutes. Mixture from the tank 26 is pumped by a low-shear pump 30 such as a mono pump to a tangential inlet of a second fluidic vortex mixer 32; a buffer solution of sodium acetate and acetic acid is pumped from a storage tank 34 by a pump 36 to another tangential inlet of the fluidic vortex mixer 32, and the resulting mixture is supplied to a tank 40. The buffer solution lowers the pH of the mixture to about pH 3.5, and the complexes consequently precipitate. As with the mixer 18, the mixing process in the mixer 32 takes place rapidly, and the residence time is less than the induction time for precipitation to commence so that there is no tendency for fouling due to proteinaceous deposits in the mixer 32.

The mixture from the tank 40 is then supplied to a centrifuge 42, such as a disk stack centrifuge, to separate the precipitate (which contains proteins and precipitated open-strand chromosomal DNA and host-cell RNA) from the supernatant liquid (which contains the plasmid DNA).

It will be appreciated that the system 10 can be modified in various ways while remaining within the scope of the present invention. For example, the cells from the cell fermentation tank 12 might be separated from the aqueous fermentation medium by centrifuging, and then resuspended in an appropriate aqueous solution, before being supplied to the fluidic vortex mixer 18. Alternatively, in the system 10, the pump 16 might be omitted and the cell suspension supplied directly to the vortex mixer 18 as a result of gas pressure or hydrostatic pressure in the tank 12. The tank 26 in which lysis is completed may be provided with an impeller, and indeed may be subdivided axially into successive cells with a common impeller, to provide better control over the residence time. In a further alternative, the buffer solution from the tank 34 (which causes precipitation) might instead be supplied through a capillary tube (not shown) into the outlet duct 24 so as to feed the buffer solution directly into the swirling liquid near the axis of the duct 24; the duct 24 can then be connected directly to the precipitation tank 40. This enables the cell walls to be broken down, but prevents the subsequent unravelling of the cell contents and the consequential increase in viscosity from occurring.

I claim:

1. A method for processing cells wherein an aqueous suspension of cells is intimately mixed with a lysis reagent by passage through a mixer, the mixer being a fluidic vortex mixer comprising a substantially cylindrical chamber with an axial outlet at the centre of an end wall of the chamber, and with at least two inlets at or near the periphery of the chamber, at least one inlet being substantially tangential so as to cause spiralling flow in the chamber, the chamber containing no baffles, and the dimensions of the mixer and the flow rates being such that the residence time of the cell suspension in the mixer is less than the time for lysis to be completed.

2. A method as claimed in claim 1 wherein the residence time is sufficiently short that the viscosity of the mixture increases by a factor of less than two during passage through the vortex mixer.

3. A method as claimed in claim 1 wherein the residence time is less than 0.01 seconds.

4. A method as claimed in claim 1 wherein the mixture of cell suspension and lysis reagent is subsequently mixed with a precipitation agent by passage through a second fluidic vortex mixer.

5. A method as claimed in claim 1 wherein a precipitation agent is injected into the mixture of cell suspension and lysis reagent within the outlet from the fluidic vortex mixer.

6. A method as claimed in claim 5 wherein means are provided to adjust the position, within the outlet from the fluidic vortex mixer, at which the injection occurs.

7. A method for processing cells wherein an aqueous suspension of cells is intimately mixed with a lysis reagent by passage through a mixer, the mixer being a fluidic vortex mixer comprising a chamber with an outlet and at least two inlets, the chamber containing no baffles and the inlets and outlet being arranged for causing spiral flow through the chamber, and the dimensions of the mixer and the flow rates being such that the residence time of the cell suspension in the mixer is less than the time for lysis to be completed.

8. A method as claimed in claim 7 wherein the residence time is less than 0.1 second.

9. A method as claimed in claim 8 wherein the residence time is less than 0.01 second.

10. A method as claimed in claim 7 wherein the residence time is sufficiently short that the viscosity of the mixture increases by a factor of less than two during passage through the vortex mixer.

11. A method as claimed in claim 7 wherein the mixture of cell suspension and lysis reagent is subsequently mixed with a precipitation agent by passage through a second fluidic vortex mixer.

12. A method as claimed in claim 7 wherein a precipitation agent is injected into the mixture of cell suspension and lysis reagent within the outlet from the fluidic vortex mixer.

13. A method as claimed in claim 12 wherein means are provided to adjust the position, within the outlet from the fluidic vortex mixer, at which the injection occurs.

* * * * *